United States Patent [19]

Stewart et al.

[11] 4,371,944
[45] Feb. 1, 1983

[54] ETHYLENE PROCESS CONTROL

[75] Inventors: William S. Stewart; Gary L. Funk; Dexter E. Smith, all of Bartlesville, Okla.

[73] Assignee: Phillips Petroleum Company, Bartlesville, Okla.

[21] Appl. No.: 225,508

[22] Filed: Jan. 16, 1981

[51] Int. Cl.³ .......................... G06F 15/46; C10G 9/36
[52] U.S. Cl. .................................... 364/502; 364/148; 208/130; 208/DIG. 1; 422/62; 585/650; 436/55
[58] Field of Search ............... 364/502, 500, 501, 503, 364/105, 148; 585/648, 650, 652, 501; 23/230 A; 422/62, 109, 110, 119; 208/106, 130, DIG. 1

[56] References Cited
U.S. PATENT DOCUMENTS

| | | | |
|---|---|---|---|
| 3,760,168 | 9/1973 | Boyd | 364/500 |
| 4,096,574 | 6/1978 | Christie | 364/501 |
| 4,187,542 | 2/1980 | Ball et al. | 364/502 |
| 4,231,753 | 11/1980 | Stewart | 364/500 X |
| 4,318,178 | 3/1982 | Stewart et al. | 364/502 |

Primary Examiner—Edward J. Wise

[57] ABSTRACT

The heat supplied to an ethylene process cracking furnace is manipulated so as to maintain a desired ethylene production rate while the flow of feed to the ethylene process cracking furnace is manipulated so as to substantially maximize the selectivity of the ethylene process cracking furnace to the production of ethylene. In this manner a desired ethylene production rate is maintained while the process economics are improved in the case where the cost of the feed is a more important economic consideration than the cost of the energy required for the cracking furnace by substantially minimizing the conversion of the feed to undesired by-products.

14 Claims, 3 Drawing Figures

4,371,944

ETHYLENE PROCESS CONTROL

This invention relates to control of a process for producing ethylene. In a particular aspect, this invention relates to method and apparatus for controlling the ethylene production rate while substantially maximizing the selectivity of the ethylene process cracking furnace to the production of ethylene.

In a process for producing ethylene, an ethane feed stream or other suitable feed stream is fed into a cracking furnace. Within the cracking furnace the feed gas is converted to a gaseous mixture. If the feed gas is ethane, the gaseous mixture will primarily contain hydrogen, methane, acetylene, ethylene, and ethane. At the furnace exit this mixture is cooled and compressed. The compressed mixture is routed through various distillation columns where the individual components such as ethylene are purified and separated. The separated products, of which ethylene is the major product, then leave the ethylene plant to be used in numerous other processes for the manufacture of a wide variety of secondary products.

As used herein the term "conversion" refers to the number of moles of feed ethane which are cracked in one pass through the cracking furnace. The term "selectivity" refers to the number of moles of ethylene flowing from a cracking furnace divided by the number of moles of ethylene plus methane and acetylene. The term "severity equivalent" refers to the ratio of two constituents in the product stream flowing through the cracking furnace. A commonly used ratio is the ratio of methane to ethylene. The severity equivalent is directly related to selectivity and may be utilized as an indication of selectivity.

A number of considerations must be taken into account in determining the manner in which an ethylene process will be operated and controlled. A primary concern in how much ethylene is being produced. However, the amount of feed and energy required to produce a given quantity of ethylene must be considered. If the feed is a more relevant cost consideration than energy, then process economics are maximized by maximizing the selectivity of the cracking furnace to the production of ethylene while still providing some desired ethylene production rate for the overall ethylene process. This reduces the production of methane and acetylene but results in higher energy cost since converstion must be lowered to maximize selectivity.

It is thus an object of this invention to provide method and apparatus for controlling an ethylene manufacturing process so as to provide a desired ethylene production rate while substantially maximizing the selectivity of ethylene process cracking furnace to the production of ethylene.

In accordance with the present invention the heat supplied to a cracking furnace is manipulated so as to maintain a desired ethylene production rate while the flow of feed to the cracking furnace is manipulated so as to substantially maximize the selectivity of the ethylene process cracking furnace to the production of ethylene. In this manner a desired ethylene production rate is maintained while the process economics are improved in the case where the cost of the feed is more important economic consideration than the cost of the energy required for the cracking furnace by substantially minimizing the conversion of the feed to undesired by-products.

In general, the control of the heat supplied to the cracking furnace may be accomplished by deriving a set point for the heat to be supplied to the cracking furnace based on a comparison of the actual ethylene production rate to a desired ethylene production rate. The thus derived set point may be compared to the actual heat being supplied to the cracking furnace to derive a control signal which may be utilized to manipulate the heat being supplied to the cracking furnace so as to force the heat supplied to the cracking furnace to a level which will provide the desired ethylene production rate.

The flow of feed to the cracking furnace may be manipulated by comparing an actual severity equivalent to a desired severity equivalent. Constraint control may also be utilized to ensure that control based on the desired severity equivalent will not violate a process constraint. The comparison of the desired severity equivalent to the actual severity equivalent may then be utilized to manipulate the flow of feed to the cracking furnace so as to manitain a desired severity equivalent which will substantially maximize the selectivity of the ethane cracking furnace to the production of ethylene.

Other objects and advantages of the invention will be apparent from the foregoing brief description of the invention and the claims as well as the detailed description of the drawings in which:

The invention is described in terms of utilizing an ethylene feed to produce ethylene. However, the invention is also applicable to utilizing other feeds such as propane, naphthas or gas oils which produce additional products. The principle of utilizing the heat input to the cracking furnace to maintain a desired ethylene production rate and utilizing the feed flow rate to the cracking furnace to maintain a desired selectivity to the production of ethylene would remain the same.

Figure 1:
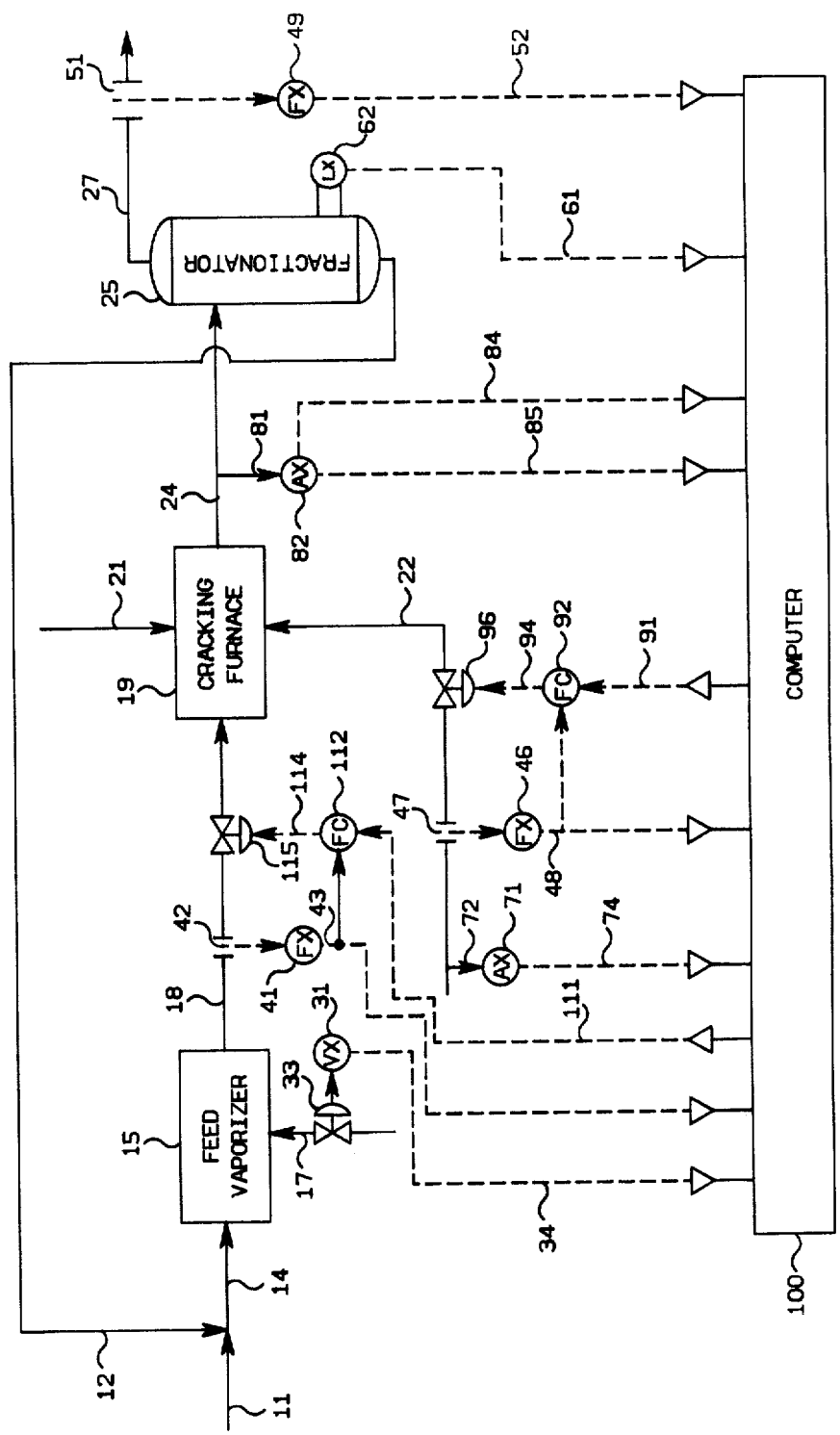
FIG. 1 is a diagrammatic illustration of an ethylene process together with the control system of the present invention for the ethylene process.

Only the parts of the ethylene process and the control elements for the ethylene process required to illustrate the present invention are illustrated in FIG. 1 for the sake of simplicity. A large amount of process control equipment other than that illustrated in FIG. 1 would be utilized to control a complete ethylene process. Also additional equipment such as pumps, heat exchangers and additional vessels would be utilized. However, the additional equipment required is well known and has been used for many years in ethylene processes.

A specific control system configuration is set forth in FIG. 1 for the sake of illustration. However, the invention extends to different types of control system configurations which accomplish the purpose of the invention. Lines designated as signal lines in the drawings are electrical or pneumatic in this preferred embodiment. Generally, the signals provided from any transducer are electrical in form. However, the signals provided from flow sensors will generally be pneumatic in form. Transducing of these signals is not illustrated for the sake of simplicity because it is well known in the art that if a flow is measured in pneumatic form it must be transduced to electrical form if it is to be transmitted in electrical form by a flow transducer. Also, transducing of the signals from analog form to digital form or from digital form to analog form is not illustrated because such transducing is also well known in the art.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

A digital computer is used in the preferred embodiment of this invention to calculate the required control signals based on measured process parameters as well as set points supplied to the computer. Analog computers or other types of computing devices could also be used in the invention. The digital computer is preferably an OPTROL 7000 Process Computer System for Applied Automation, Inc., Bartlesville, Okla.

Both the analog and digital controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention. The operation of proportional-integral-derivative controllers is well known in the art. The output control signal of a proportional-integral-derivative controller may be represented as $$S = K_1 E + K_2 \int E dt + K_3 dE/dt$$

where

S = output control signals;
E = difference between two input signals; and $K_1$, $K_2$ and $K_3$ = constants.

The scaling of an output signal by a controller is well known in control systems art. Essentially, the output of a controller may be scaled to represent any desired factor or variable. An example of this is where a desired flow rate and an actual flow rate is compared by a controller. The output could be a signal representative of a desired change in the flow rate of some gas necessary to make the desired and actual flows equal. On the other hand, the same output signal could be scaled to represent a percentage or could be scaled to represent a temperature change required to make the desired and actual flows equal. If the controller output can from 0 to 10 volts, which is typical, then the output signal could be scaled so that an output signal having a voltage level of 5.0 volts correspond to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more of such equipment types. While the presently preferred embodiment of the invention preferably utilizes a combination of pneumatic final control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relaionship to the measured parameter. Regardless of the signal format or the exact relationship of the signal to the parameter which it represents, each signal representative of a measured process parameter or representative of a desired process value will bear a relationship to the measured parameter or desired value which permits designation of a specific or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to the drawings and in particular to FIG. 1, a fresh ethane feedstock is supplied through conduit means 11. The fresh feedstock flowing through conduit means 11 is combined with a recycle ethane flowing through conduit means 12 and the combined feed is supplied through conduit means 14 to the feed vaporizer 15. A heating fluid is provided to the feed vaporizer 15 through conduit means 17. A burner may be utilized to supply the heat required to vaporize the feed if desired and if a burner is utilized fuel would be supplied through conduit means 17.

The feed flowing through conduit means 14 is substantially vaporized in the feed vaporizer 15 and is provided through conduit means 18 to the cracking furnace 19. Steam is provided to the cracking furnace 19 through conduit means 21. Fuel is supplied to burners in the cracking furnace through conduit means 22. The feed stream flowing through conduit means 18 and the steam flowing through conduit means 21 are combined within the cracking furnace 19 and flow through cracking tubes which are heated by burners supplied with fuel through conduit means 22. After passing through the cracking tubes in which a portion of the feed gas is converted to ethylene, methane, hydrogen, and acetylene, the resulting gaseous mixture is withdrawn from the cracking furnace 19 through conduit means 24. The processing of the gaseous mixture flowing through conduit means 24 will consist of a number of steps such as cooling, compression, and acetylene removal. However, the primary step of interest is the separation of ethylene from the ethane remaining in the feed and thus this is the only step illustrated.

The gaseous mixture flowing through conduit means 24 is provided, after conventional processing, as a feed to the fractional distillation column 25. The overhead product from the fractional distillation column 25, which will be a high purity ethylene product, is removed through conduit means 27. Ethane is removed as a bottoms product from the fractional distillation column 25, is recycled through conduit means 12 and is fed to the cracking furnace 19 as has been previously described.

Valve position transducer 31 in conjunction with a device which determines the position of the control valve 33, which is operably located in conduit means 17, provides an output signal 34 which is representative of the actual position of the control valve 33. Signal 34 is provided from the valve position transducer 31 as an input signal to computer means 100.

The flow transducer 41, in combination with the flow sensor 42 which is operably located in conduit means 18, provides an output signal 43 which is representative of the flow rate of the feed flowing through conduit means 18. Signal 43 is provided from the flow transducer 41 as an input to computer means 100. In like manner, flow transducer 46 in conjunction with flow sensor 47 provides an output signal 48 which is representative of the flow rate of the fuel flowing through conduit means 22 as an input signal to computer means 100 and flow transducer 49 in conjunction with the flow sensor 51 provides an output signal 52 which is representative of the actual production rate of ethylene as an input to computer means 100.

Analyzer 71 is preferably a chromatographic BTU analyzer. A sample of the fuel flowing through conduit means 22 is provided to the analyzer 71 through conduit means 72. The analyzer transducer 71 provides an output signal 74 which is representative of the number of BTU's in each cubic foot of the fuel flowing through conduit means 22. Signal 74 is provided from the analyzer transducer 71 to computer means 100.

Analyzer transducer 82 is preferably a chromatographic analyzer capable of measuring the concentration of various constituents in a gaseous mixture. A sample of the gaseous mixture flowing through conduit means 24 is provided to analyzer transducer 82 through conduit means 81. Signal 84, provided from the analyzer transducer 82, is representative of the methane concentration in the gaseous mixture flowing through conduit means 24 and signal 85 is representative of the ethylene concentration. Signals 84 and 85 are provided from the analyzer transducer 82 to computer means 100.

Level transducer 62, in combination with level sensing instrumentation located in the fractional distillation column 25, provides an output signal 61 representative of the liquid level in the fractional distillation column 25. Signal 61 is provided from the level transducer 62 as an input to computer means 100.

In response to the described input signals, computer means 100 calculates the flow rate of the fuel flowing through conduit means 22 required to maintain a desired ethylene production rate and also calculates the flow rate of feed to the cracking furnace 19 required to maintain a desired severity eqivalent without violating a process constraint to thereby substantially maximize the selectivity of the cracking furnace to the production of ethylene.

Signal 91, which is representative of the desired flow rate of the fuel flowing through conduit means 22, is provided as the set point signal to the flow controller 92. The flow controller 92 is also provided with signal 48 as the process variable signal. The flow controller 92 provides an output signal 94 which is responsive to the difference between signals 48 and 91. Signal 94 is provided as a control signal to the control valve 96 which is operably located in conduit means 22. The control valve 96 is manipulated in response to signal 94 to thereby maintain the actual flow rate of the fuel flowing through conduit means 22 substantially equal to the desired flow rate of the fuel flowing through conduit means 22 as represented by signal 91.

Signal 111, which is representative of the desired flow rate of the feed flowing through conduit 18, is provided as a set point signal to the flow controller 112. The flow controller 112 is also provided with signal 43 as the process variable input. The flow controller 112 establishes an output signal 114 which is responsive to the difference between signals 111 and 43. Signal 114 is scaled so as to be representative of the position of the control valve 115 required to maintain the actual flow rate of the feed flowing through conduit means 18 substantially equal to the desired flow rate represented by signal 111. Signal 114 is provided as a control signal to the control valve 115 which is operably located in conduit means 18. The control valve 115 is manipulated in response to signal 114 to thereby maintain the actual flow rate of the feed flowing through conduit means 18 substantially equal to the desired flow rate.

Figure 2:
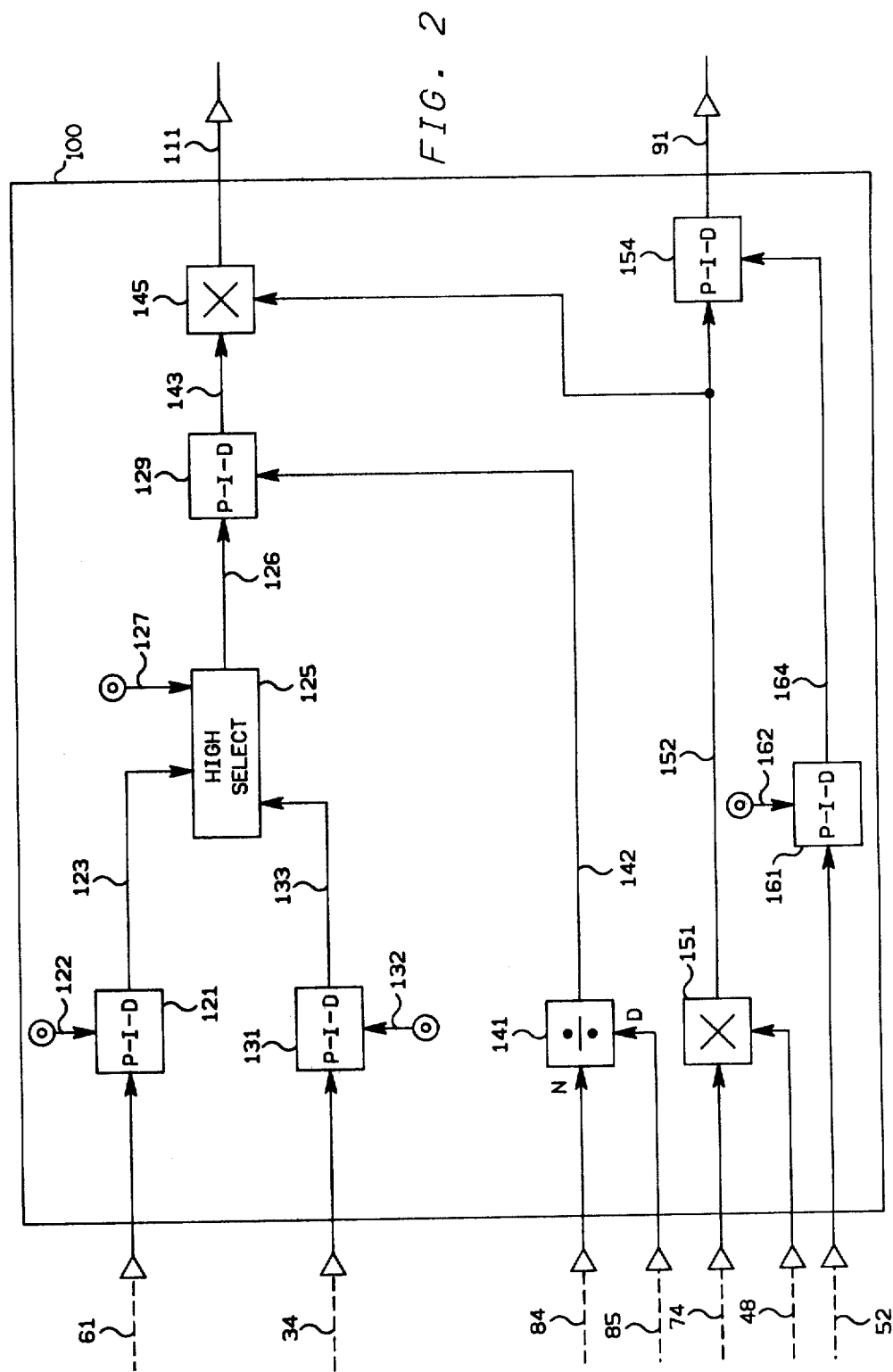
FIG. 2 is a logic diagram of the computer logic utilized to generate the control signals illustrated in FIG. 1 based on the process measurements.

The logic flow diagram utilized to calculate the control signals 91 and 111 in response to the previously described input signals to computer means 100 is illustrated in FIG. 2. Referring now to FIG. 2, computer means 100 is shown as a solid line surrounding the logic flow.

The high select block 125 is utilized to establish signal 126 which is representative of the desired severity equivalent for the gaseous mixture flowing through conduit means 24. The set point signal 127, which is provided to the high select 125, is representative of a severity equivalent which will provide the desired maximization of the selectivity of the cracking furnace 19 to the production of ethylene. Signal 127 could be provided directly as signal 126 to the proportional-integral-derivative (P-I-D) block 129. However, to substantially maximize selectivity, conversion must be reduced. This requires that the flow rate of the feed to the cracking furnace must be increased which results in an increased production of ethane. This affects the level of the liquid in the bottom of the fractional distillation column utilized to separate the ethylene from ethane and also results in an increased recycle of ethane. Because of these factors, it is desirable to utilize constraint control to prevent the value of signal 126 from forcing the feed rate to a point which would violate a process constraint such as liquid level in the distillation column being utilized to separate the ethylene from ethane.

A first constraint is established by providing signal 61, which is representative of the actual liquid level in the fractional distillation column 25, to the P-I-D block 121. The P-I-D block 121 is also provided with signal 122 which is representative of a high limit on the liquid level in the distillation column. P-I-D block 121 establishes signal 123 which is responsive to the difference between signals 61 and 122. Signal 123 is provided as an input to the high select 125. Signal 123 is scaled so as to be representative of the lowest severity equivalent which may be attained without exceeding the high limit represented by signal 122.

A second constraint is established to prevent a limitation on the amount of heating fluid which can be provided through conduit means 17 from being exceeded. Signal 34, which is representative of the actual valve position of the control valve 33, is provided as the process variable input to the P-I-D block 131. Signal 132, which is representative of a high limit on the valve position of the control valve 33, is provided as the set point input to the P-I-D block 131. The P-I-D block 131 establishes signal 133 which is responsive to the difference between signals 34 and 132. Signal 133 is provided from the P-I-D block 131 as an input to the high select 125. Signal 133 is scaled so as to be representative of the lowest severity equivalent which may be achived without exceeding a limitation on the amount of heating fluid which can be provided through conduit means 17.

The highest of signals 123, 127 and 133 is provided as signal 126 from the high select 125. In general, signal 127 is provided as signal 126 unless a process constraint would be violated in which case either signal 123 or signal 133 will be provided as signal 126.

Other process limitations such as low limits on the flow rate of steam flowing through conduit means 21 and the pressure of the gaseous mixture flowing through conduit means 24 or a high limit on the acetylene concentration in the gaseous mixture flowing through conduit means 24 may also be utilized if desired to ensure that the desired severity equivalent represented by signal 126 does not require a feed flow rate which would violate a process constraint. The two process constraints described are illustrative of constraint control which is applicable to the present invention and are utilized because these two constraints are particularly applicable to the present invention in which the feed flow rate is being manipulated so as to maintain a desired severity equivalent.

Signal 84, which is representative of the concentration of methane in the gaseous mixture flowing through conduit means 24, is provided to the numerator input of the dividing block 141. Signal 85, which is representative of the concentration of ethylene in the gaseous mixture flowing through conduit means 24, is provided to the denominator input of the dividing block 141. Signal 142, which is representative of the actual severity equivalent for the gaseous mixture flowing through conduit means 24, is provided from the dividing block 141 as the process variable input to the P-I-D block 129. The P-I-D block 129 establishes signal 143 which is responsive to the difference between signals 126 and 142. Signal 143 is scaled so as to be representative of the number of pounds of feed which must be provided to the cracking furnace 19 for each BTU provided to the cracking furnace 19 to maintain the actual severity equivalent substantially equal to the desired severity equivalent. Signal 143 is provided from the P-I-D block 129 as an input to the multiplying block 145.

Signal 74, which is representative of the BTU's which can be provided by combusting a cubic foot of the fuel flowing through conduit means 22, is provided as a first input to the multiplying block 151. Signal 48, which is representative of the flow rate in cubic feet per hour of the fuel flowing through conduit means 22, is provided as a second input to the multiplying block 151. Signal 152, which is representative of the number of BTU's being provided to the cracking furnace 19 per hour, is provided from the multiplying block 151 as an input to the multiplying block 145 and as the process variable input to the P-I-D block 154.

Signal 143 is multiplied by signal 152 to establish signal 111 which is representative of the number of pounds of feed which must be provided to the cracking furnace 19 per hour to maintain the actual severity equivalent for the gaseous mixture flowing through conduit means 24 substantially equal to the desired severity equivalent. Signal 111 is provided as an output signal from computer means 100 and is utilized as has been previously described.

Signal 52, which is representative of the actual ethylene production rate, is provided as the process variable input to the P-I-D block 161. The P-I-D block 161 is also provided with a set point signal 162 which is representative of the desired ethylene production rate. The P-I-D block 161 establishes an output signal 164 which is responsive to the difference between signals 52 and 162. Signal 164 is scaled so as to be representative of the number of BTU's per hour which must be provided to the cracking furnace 19 to maintain a desired ethylene production rate. Signal 164 is provided from the P-I-D block 161 as the set point input to the P-I-D block 154. The P-I-D block 154 establishes signal 91 which is responsive to the difference between signals 152 and 164. Signal 91 is provided as an output signal from computer means 100 and is utilized as has been previously described.

Figure 3:
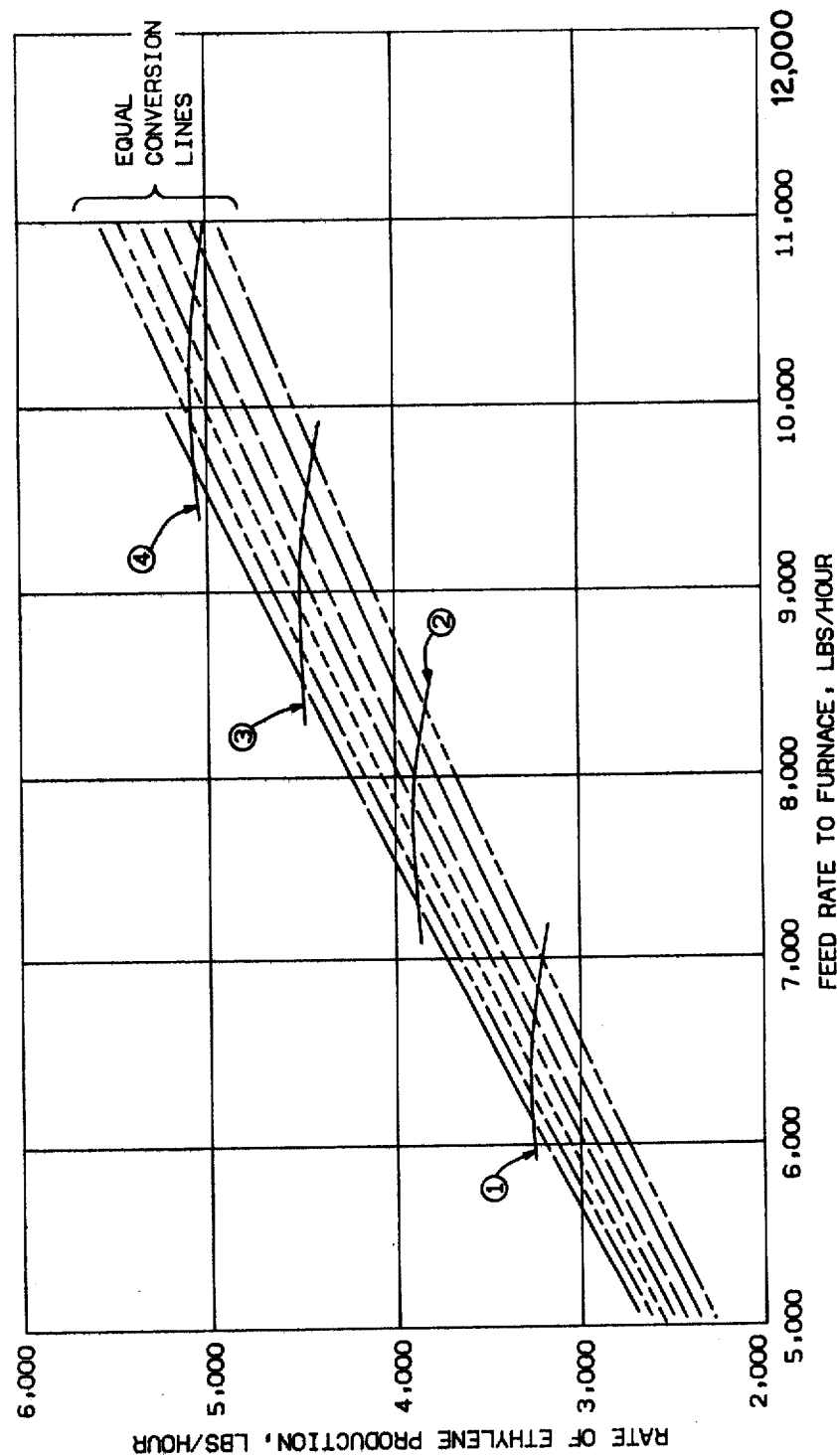
FIG. 3 is a graphical illustration of the effect of heat input to the cracking furnace and hydrocarbon feed rate to the cracking furnace on ethylene production.

Referring now to FIG. 3, there is illustrated a plot of rate of ethylene production, as represented by signal 52, as a function of the hydrocarbon feed rate, as represented by signal 43. The lines extending diagonally across the plot are equal-conversion lines. Lines 1, 2, 3 and 4 are equal-heat input lines. Thus, all points on line 1 represent the same heat input to the cracking furnace 19 with line 4 being the highest heat input and line 1 being the lowest. As is illustrated in FIG. 3, the ethylene production rate is virtually independent of the hydrocarbon feed rate. Thus, signal 91 may be utilized to control the ethylene production rate by manipulating the heat supplied to the cracking furnace. At the same time the conversion may be lowered without substantially affecting the ethylene production rate which allows selectivity to the production of ethylene to be substantially maximized.

The invention has been described in terms of a preferred embodiment as illustrated in FIGS. 1 and 2. Specific control components which can be used in the practice of the invention as illustrated in FIG. 1 such as flow sensors 42, 47 and 51; flow transducers 41, 46 and 49; valve position transducer 31; flow controllers 92 and 112; and control valves 33, 115 and 96 are each well known, commercially available control components such as are illustrated and described at length in Perry's *Chemical Engineer's Handbook*, 4th Edition, Chapter 22, McGraw-Hill. A suitable analyzer which may be utilized for the BTU analyzer 71 and the chromatographic analyzer 81 is the process chromatograph system, model 102, manufactured by Applied Automation, Inc., Bartlesville, Okla.

While the invention has been described in terms of the presently preferred embodiment, reasonable variations and modifications are possible by those skilled in the art as has been discussed. Such variations and modifications are within the scope of the described invention and the appended claims.

That which is claimed is:

1. Apparatus comprising:

a cracking furnace means;

means for supplying a feed stream to said cracking furnace means;

means for supplying a diluent fluid to said cracking furnace means, said diluent fluid being combined with said feed stream;

means for supplying a fuel to said cracking furnace means, the combustion of said fuel supplying heat to said cracking furnace means;

a fractional distillation column means;

means for removing a gaseous mixture, containing the cracked components of said feed stream and containing said diluent fluid, from said cracking furnace means and for providing desired components of said gaseous mixture as a feed to said fractional distillation column means;

means for removing an overhead stream containing ethylene from said fractional distillation column means;

means for establishing a first signal representative of the actual flow rate of said overhead stream;

means for establishing a second signal representative of the desired flow rate of said overhead stream;

means for comparing said first signal and said second signal and for establishing a third signal responsive to the difference between said first signal and said second signal;

means for establishing a fourth signal representative of the actual heat being supplied to said cracking furnace means;

means for comparing said third signal and said fourth signal and for establishing a fifth signal which is responsive to the difference between said third signal and said fourth signal;

means for manipulating the heat input to said cracking furnace means in response to said fifth signal;

means for establishing a sixth signal representative of the ratio of the concentration of an undesired component in said gaseous mixture to the concentration of ethylene in said gaseous mixture (severity equivalent);

means for establishing a seventh signal representative of the desired severity equivalent;

means for comparing said sixth signal and said seventh signal and for establishing an eighth signal responsive to the difference between said sixth signal and said seventh signal; and means for manipulating the flow rate of said feed stream to said cracking furnace means in response to said eighth signal.

2. Apparatus in accordance with claim 1 wherein said third signal is scaled so as to be representative of the heat which must be supplied to said cracking furnace means to maintain the actual flow rate of said overhead stream substantially equal to the desired flow rate as represented by said second signal and wherein said means for establishing said fourth signal comprises:

means for establishing a ninth signal representative of the number of BTU's which may be obtained by combusting a unit volume of said fuel;

means for establishing a tenth signal representative of the flow rate of said fuel; and means for multiplying said eighth signal by said ninth signal to establish said fourth signal.

3. Apparatus in accordance with claim 2 wherein said fifth signal is scaled so as to be representative of the flow rate of said fuel required to maintain the actual heat supplied to said cracking furnace means substantially equal to the desired heat represented by said third signal and wherein said means for manipulating the heat input to said cracking furnace means in response to said fifth signal comprises:

means for comparing said fifth signal and said tenth signal and for establishing an eleventh signal responsive to the difference between said fifth signal and said tenth signal; and means for manipulating the flow rate of said fuel in response to said eleventh signal.

4. Apparatus in accordance with claim 2 wherein said eighth signal is scaled so as to be representative of the number of pounds of feed which must be supplied to said cracking furnace means for each unit of heat supplied to said cracking furnace means to maintain said sixth signal substantially equal to said seventh signal and wherein said means for manipulating the flow of feed to said cracking furnace means in response to said eighth signal comprises:

means for multiplying said eighth signal by said fourth signal to establish an eleventh signal representative of the required flow rate of said feed;

means for establishing a twelfth signal representative of the actual flow rate of said feed;

means for comparing said eleventh signal and said twelfth signal and for establishing a thirteenth signal responsive to the difference between said eleventh signal and said twelfth signal; and means for manipulating the flow rate of said feed in response to said thirteenth signal.

5. Apparatus in accordance with claim 1 wherein said undesired component is methane and said means for establishing said sixth signal comprises:

means for analyzing said gaseous mixture to determine the concentration of methane in said gaseous mixture and the concentration of ethylene in said gaseous mixture; and means for dividing the concentration of methane by the concentration of ethylene to establish said sixth signal.

6. Apparatus in accordance with claim 1 wherein said means for supplying said feed stream to said cracking furnace means comprises:

a feed vaporizer means;

means for supplying a fresh feed stream to said feed vaporizer means;

means for supplying a bottoms stream from said fractional distillation column means to said feed vaporizer means; and means for providing a combined fresh feed streams and bottoms stream from said feed vaporizer means to said cracking furnace means.

7. Apparatus in accordance with claim 6 wherein said means for establishing said seventh signal comprises:

means for establishing a ninth signal representative of the severity equivalent required to substantially maximize the selectivity of said cracking furnace means to the production of ethylene;

means for establishing a tenth signal representative of the lowest severity equivalent which may be achieved without exceeding a high limit for liquid level in the bottom of said fractional distillation column means;

means for establishing an eleventh signal representative of the lowest severity equivalent which may be achieved without exceeding a high limit on the amount of heat which can be provided to said feed vaporizer; and means for selecting the higher of said ninth, tenth and eleventh signals to establish said seventh signal.

8. A method for maintaining a desired ethylene production rate and a desired ratio of the concentration of an undesired component in the gaseous mixture flowing from the ethylene process cracking furnace to the concentration of ethylene in said gaseous mixture (severity equivalent) for an ethylene process in which a mixture of a feed stream and a diluent fluid are cracked in said cracking furnace to produce said gaseous mixture which contains the cracked components of said feed stream and contains said diluent fluid and in which ethylene is separated from said gaseous mixture by fractional distillation to provide an ethylene-containing stream, said method comprising the steps of:

establishing a first signal representative of the actual flow rate of said ethylene containing stream;

establishing a second signal representative of the desired flow rate of said ethylene containing stream;

comparing said first signal and said second signal and establishing a third signal responsive to the difference between said first signal and said second signal;

establishing a fourth signal representative of the actual heat being supplied to said cracking furnace;

comparing said third signal and said fourth signal and for establishing a fifth signal which is responsive to the difference between said third signal and said fourth signal;

manipulating the heat input to said cracking furnace in response to said fifth signal;

establishing a sixth signal representative of the actual severity equivalent;

establishing a seventh signal representative of the desired severity equivalent;

comparing said sixth signal and said seventh signal and for establishing an eighth signal responsive to the difference between said sixth signal and said seventh signal; and manipulating the flow rate of said feed stream to said cracking furnace in response to said eighth signal.

9. A method in accordance with claim 8 wherein said third signal is scaled so as to be representative of the heat which must be supplied to said cracking furnace to maintain the actual flow rate of said ethylene containing stream substantially equal to the desired flow rate as represented by said second signal, wherein a fuel is supplied to said cracking furnace with the combustion of said fuel supplying heat to said cracking furnace and wherein said step of establishing said fourth signal comprises:

establishing a ninth signal representative of the number of BTU's which may be obtained by combusting a unit volume of said fuel;

establishing a tenth signal representative of the flow rate of said fuel; and multiplying said eighth signal by said said ninth signal to establish said fourth signal.

10. A method in accordance with claim 9 wherein said fifth signal is scaled so as to be representative of the flow rate of said fuel required to maintain the actual heat supplied to said cracking furnace means substantially equal to the desired heat represented by said third signal and wherein said step of manipulating the heat input to said cracking furnace in response to said fifth signal comprises:

comparing said fifth signal and said tenth signal and establishing an eleventh signal responsive to the difference between said fifth signal and said tenth signal; and manipulating the flow rate of said fuel in response to said eleventh signal.

11. A method in accordance with claim 9 wherein said eighth signal is scaled so as to be representative of the number of pounds of feed which must be supplied to said cracking furnace for each unit of heat supplied to said cracking furnace to maintain said sixth signal substantially equal to said seventh signal and wherein said step of manipulating the flow of feed to said cracking furnace in response to said eighth signal comprises:

multiplying said eighth signal by said fourth signal to establish an eleventh signal representative of the required flow rate of said feed;

establishing a twelfth signal representative of the actual flow rate of said feed;

comparing said eleventh signal and said twelfth signal and establishing a thirteenth signal responsive to the difference between said eleventh signal and said twelfth signal; and manipulating the flow rate of said feed in response to said thirteenth signal.

12. A method in accordance with claim 8 wherein said undesired component is methane and said step of establishing said sixth signal comprises:

analyzing said gaseous mixture to determine the concentration of methane in said gaseous mixture and the concentration of ethylene in said gaseous mixture; and dividing the concentration of methane by the concentration of ethylene to establish said sixth signal.

13. A method in accordance with claim 8 wherein said step of supplying said feed stream to said cracking furnace comprises:

combining a fresh feed stream with a bottoms stream provided from said fractional distillation process to produce a combined feed stream;

vaporizing said combined feed stream; and supplying the vaporized combined feed stream to said cracking furnace.

14. A method in accordance with claim 13 wherein said step of establishing said seventh signal comprises:

establishing a ninth signal representative of the severity equivalent required to substantially maximize the selectivity of said cracking furnace means to the production of ethylene;

establishing a tenth signal representative of the lowest severity equivalent which may be achieved without exceeding a high limit for the bottoms liquid level in said fractional distillation process;

establishing an eleventh signal representative of the lowest severity equivalent which may be achived without exceeding a high limit on the amount of heat which can be provided to vaporize said combined feed stream; and selecting the higher of said ninth, tenth and eleventh signals to establish said seventh signal.

* * * * *